United States Patent
Rubadou

(10) Patent No.: US 9,468,752 B2
(45) Date of Patent: Oct. 18, 2016

(54) TONGUE RELAXER

(71) Applicant: Lawrence Keith Rubadou, East Taunton, MA (US)

(72) Inventor: Lawrence Keith Rubadou, East Taunton, MA (US)

( * ) Notice: Subject to any disclaimer, the term of this patent is extended or adjusted under 35 U.S.C. 154(b) by 0 days.

(21) Appl. No.: 14/659,653

(22) Filed: Mar. 17, 2015

(65) Prior Publication Data
US 2016/0271389 A1  Sep. 22, 2016

(51) Int. Cl.
*A61N 1/00* (2006.01)
*A61N 1/05* (2006.01)
*A61N 1/36* (2006.01)
*A61N 1/08* (2006.01)

(52) U.S. Cl.
CPC ............... *A61N 1/0548* (2013.01); *A61N 1/08* (2013.01); *A61N 1/36003* (2013.01)

(58) Field of Classification Search
CPC ... A61N 1/08; A61N 1/36003; A61N 1/0548
See application file for complete search history.

(56) References Cited

U.S. PATENT DOCUMENTS

| 2009/0312817 A1* | 12/2009 | Hogle | A61B 5/0492 607/54 |
| 2010/0087896 A1* | 4/2010 | McCreery | A61F 5/566 607/62 |

* cited by examiner

*Primary Examiner* — George Manuel

(57) ABSTRACT

The Tongue Relaxer comprises of a flat body low voltage electronic therapeutic device as a precise means of releasing excessive and deep muscular restrictive muscular tension within the inside body, base, and root of the tongue. Specifically designed for Voice pedagogy, Speech therapy, Professional singers, Public speakers, however not limited to. Veterinary applications may apply as well!

Figure 1:
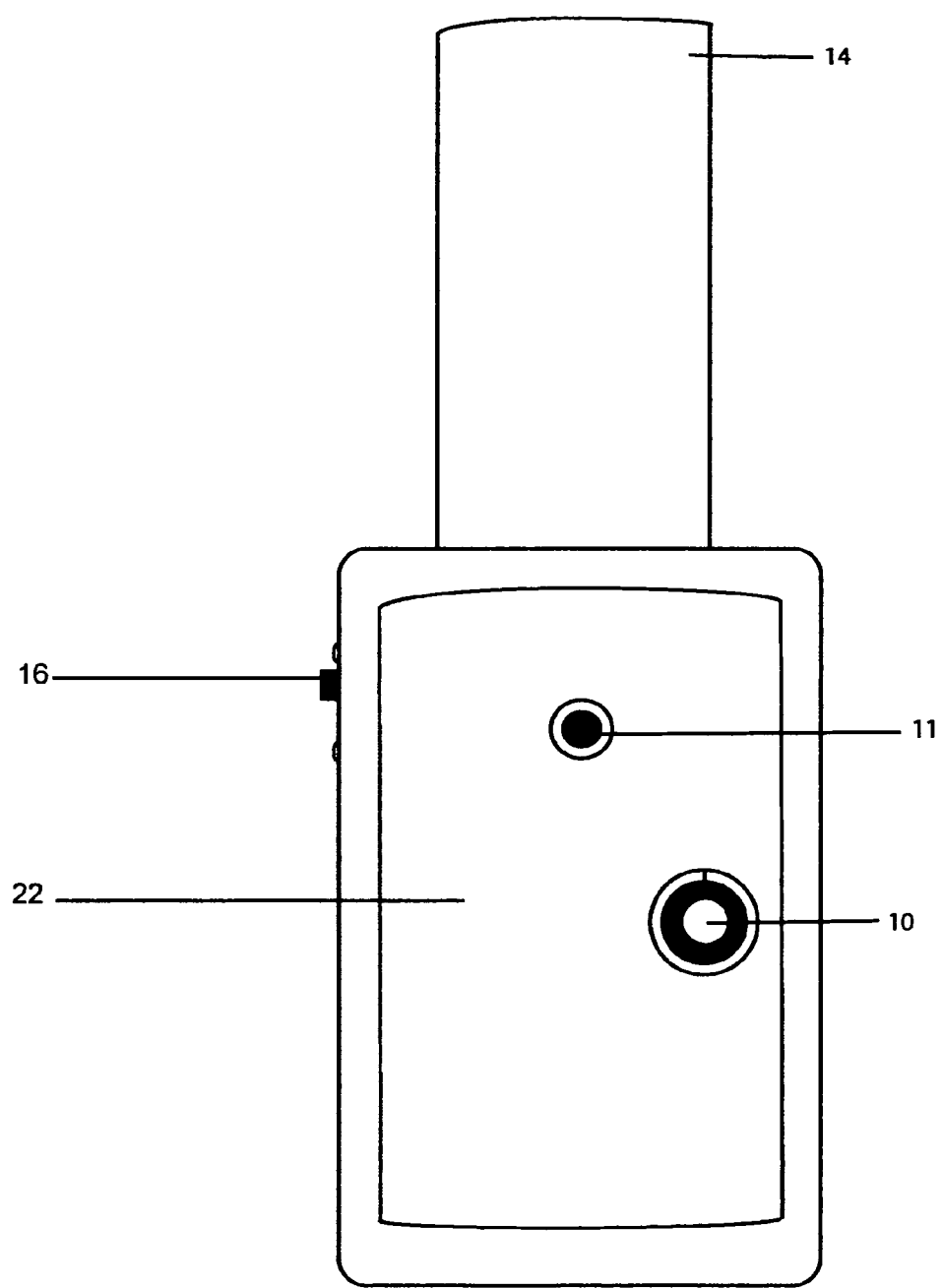

The Tongue Relaxer provides a more reliable, lightweight, yet economical device that can be used by persons of almost any age under supervision.

Working singers, actors, or public speakers often times make very unhealthy choices in a desperate attempt to temporarily relieve this tension and free there voices in order to get through a performance.

The Tongue Relaxer is an extremely quick, direct, healthy, and effective means of addressing this issue of said tongue tension that eventually effects every singer and public speaker due to sudden environmental changes such as cold and dampness. Colds, allergies and general fatigue.

3 Claims, 6 Drawing Sheets

TONGUE RELAXER

CROSS-REFERENCE TO RELATED APPLICATIONS

This application claims the benefit of non provisional application Ser. No. 14/659,653 Filed Mar. 17, 2015 by the present inventor.

FEDERAL SPONSORED RESEARCH

Not Applicable

SEQUENCE LISTING OR PROGRAM

Not Applicable

BACKGROUND

1. Field

This application relates to physical therapeutic apparatuses, specifically to such used for the tongue. This application relates to physical therapeutic apparatuses, specifically to such that are used on the tongue.

I had discovered this means of relaxing the tongue as a professional musician in the field in 1982. The typical field test for a 9 volt battery's remaining strength, was to place both contacts to the top of the tongue to test that there was adequate battery life remaining in said battery, to power a given device i.e. (guitarists effect pedal) or wireless battery pack to last through out the pending engagement. If you felt a little zap you knew that you had enough. If not, it indicated that said battery was dead. I later discovered also being a singer that my vocal performance was much freer, and less stiff when trying to reach higher notes. There was much less resistance. I found this to be a very quick, clean, and healthy means of quickly and efficiently getting the said tongue to relax and therefore the interconnected workings of the larynx.

2. Related Art

The nearest device to the tongue relaxer is the PoNs device which has several small electrodes and has a very different application. Used as only as a experimental prototype for treating MS and Parkinson's disease. This treatment takes from 20 to 30 minutes per session and operates on an automated cycle. The Tongue Relaxer however, takes only a few seconds to use and is a push button device. No prior art exists for an electronic tongue relaxer designed specifically for singers and public speakers.

Voice teachers and Voice therapists commonly in practice have traditionally used: Physical exercises, stretches, vocalizations, throat sprays, cough drops, herbal remedies, steam inhalation, steroids, smoking cigarettes, muscle relaxers, and even the consumption of alcohol and certain foods as a means to relax the tongue, throat and it's related muscles. These methods are in most cases have proven only generally effective, superficial and in many instances have accumulative detrimental health related repercussions. Many of said remedies have delayed and only general effectiveness when used as a means to address tongue tension specifically. Said muscle relaxers and or depressants also diminish a singers mental focus. Professional singers, actors, and public speakers do not have the luxury of time or ineffectiveness when deep inner tongue tension becomes an issue. It is vera serious.

Performers all have very strict schedules to keep and there are high expectations to deliver their very best every single time they step onto a stage and or podium.

Tongue tension is detrimental to all singers and public speakers who want to sing and speak correctly.

BACKGROUND—RELATED ART

Often times the effects of the prior methods is insufficient and short lived. In many instances if tension is not eradicated before a performance on the following day of a performance the subject will be left with even worse tension and therefore horsiness.

This tension is an accumulative ailment when a singer, actor, or speaker has had several consecutive performances unless tongue tension is eradicated quickly and effectively.

SUMMARY OF INVENTION

In accordance with one embodiment a Tongue Relaxer comprises of a flat body low voltage electronic therapeutic device as a precise means of releasing excessive and deep muscular restrictive tension within the inside body and base of the tongue.

Actors, and Public speakers do not have the luxury of time, Or ineffectiveness when tongue tension becomes an issue. It is very serious. Performers all have very strict schedules to keep and are expected to deliver their very best every time. Tongue tension can be detrimental to a Professional singer, actor, or Public speaker. Often times the effects of these prior methods are insufficient and short lived. In many cases if tension is not eradicated before a performance on the following day of a performance the subject will be left with even worse tension and therefore horsiness. This tension is an accumulative ailment when a singer, actor, or speaker has had several consecutive performances unless tongue tension is eradicated quickly and effectively. General fatigue and dryness or the after effects of a cold or allergies can make the tongue particularly stubborn for days or some cases even weeks.

This condition greatly inhibits the singer and or public speaker's clarity and quality of their vocal performance due to the blocking effect that said tongue will present to the vocal process if excessive tension occurs.

At times performers who are in the public eye as working singers, actors, or public speakers will often times make very unhealthy choices in a desperate attempt to temporarily relieve this tension and free there voices in order to get through a performance. Through drugs, alcohol or

SUMMARY OF INVENTION—CONTINUED

General fatigue and dryness or the after effects of a cold or allergies can make the tongue particularly stubborn for days or some cases even weeks.

This condition greatly inhibits the singer and or public speaker's clarity and quality of their vocal performance due to the blocking effect that said tongue will present to the vocal process if excessive tension occurs. Originally Therapists, Voice Teachers, Singers, Public Speakers, Sales people anyone who relies on their voice for their profession have been limited to only physical stretches, vocalizations, throat sprays, cough drops, herbal remedies, steam inhalation, even smoking, drugs and alcohol and food to relax the tongue and it's related muscles. These methods in most cases are proven to be slow acting and only generally effective forcing the singer to attempt to stretch this tension out while singing. This is awkward, unacceptable and unprofessional.

At times performers who are in the public eye as working singers, actors, or public speakers will often times make very unhealthy choices in a desperate attempt to temporarily relieve this tension in order to get through a performance. Professional singers, actors and public speakers are very aware that said tension can greatly effect a singers performance. Greatly diminishing the singers vocal range, flexibility, and tone due to the limitations of motion of the thyroid cartilage and of the contouring of deeper muscles of the tongue caused by said tongue tension.

The Tongue Relaxer is an extremely quick, direct, healthy, and effective means of addressing this issue of said tongue tension that eventually effects every singer and public speaker due t environmental changes, colds, allergies and general fatigue.

DRAWINGS

Brief Description, Several Views of the Drawings

Figure 2A:
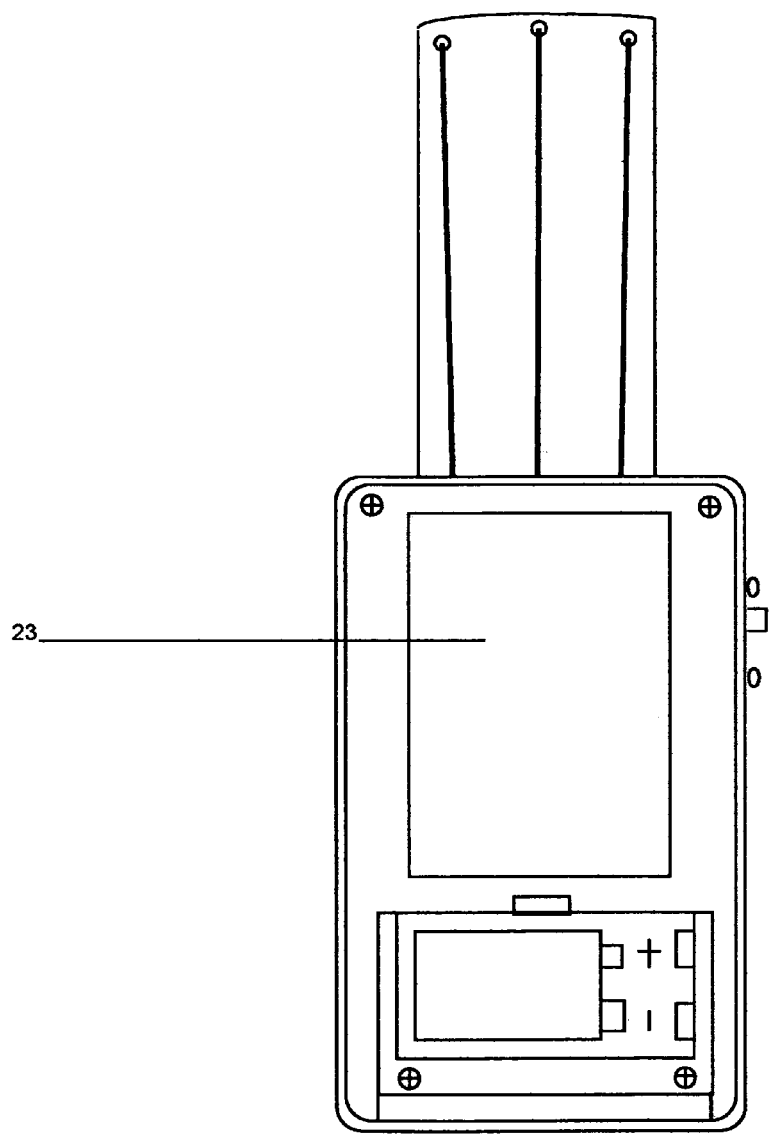
Figure 2B:
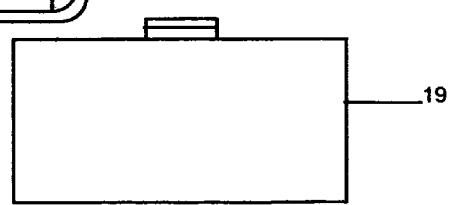
Figure 3:
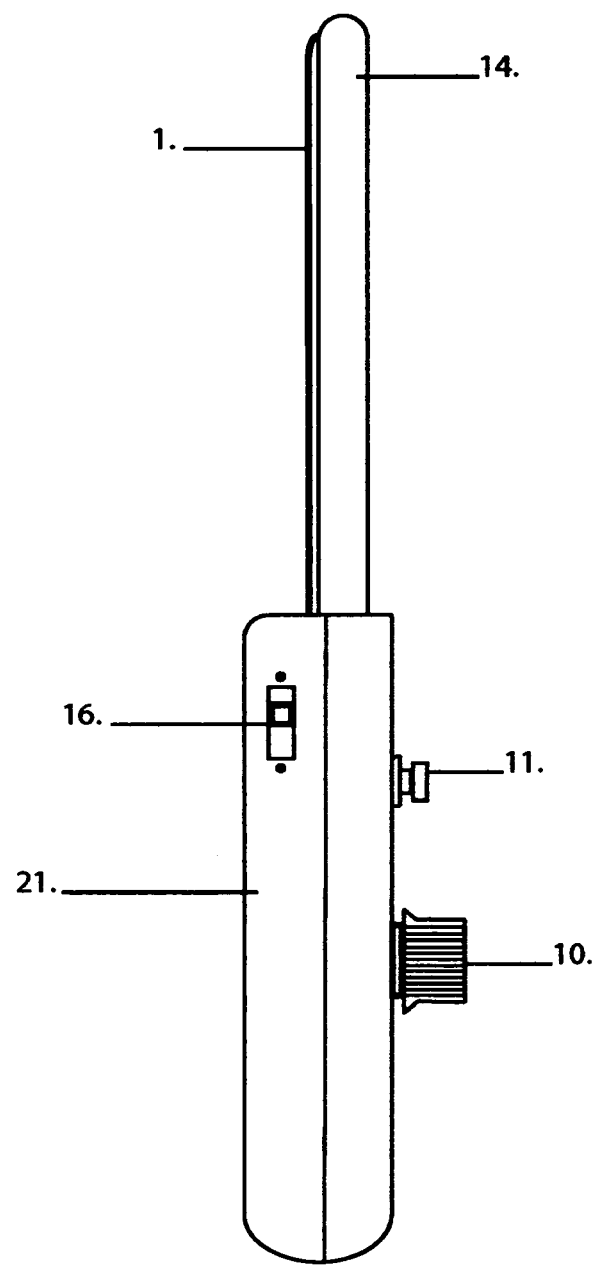
Figures 4A, 4B:
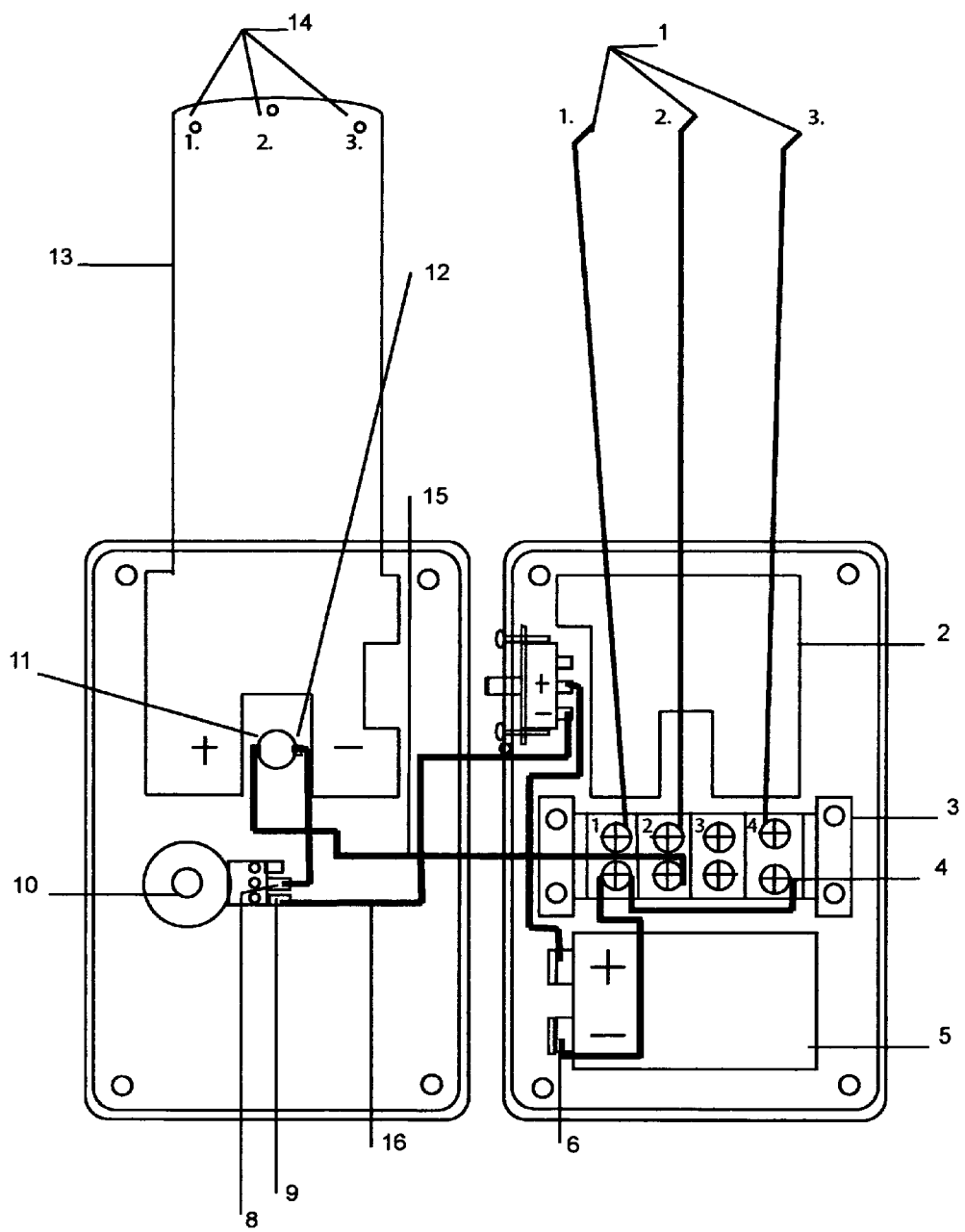
Figure 5:
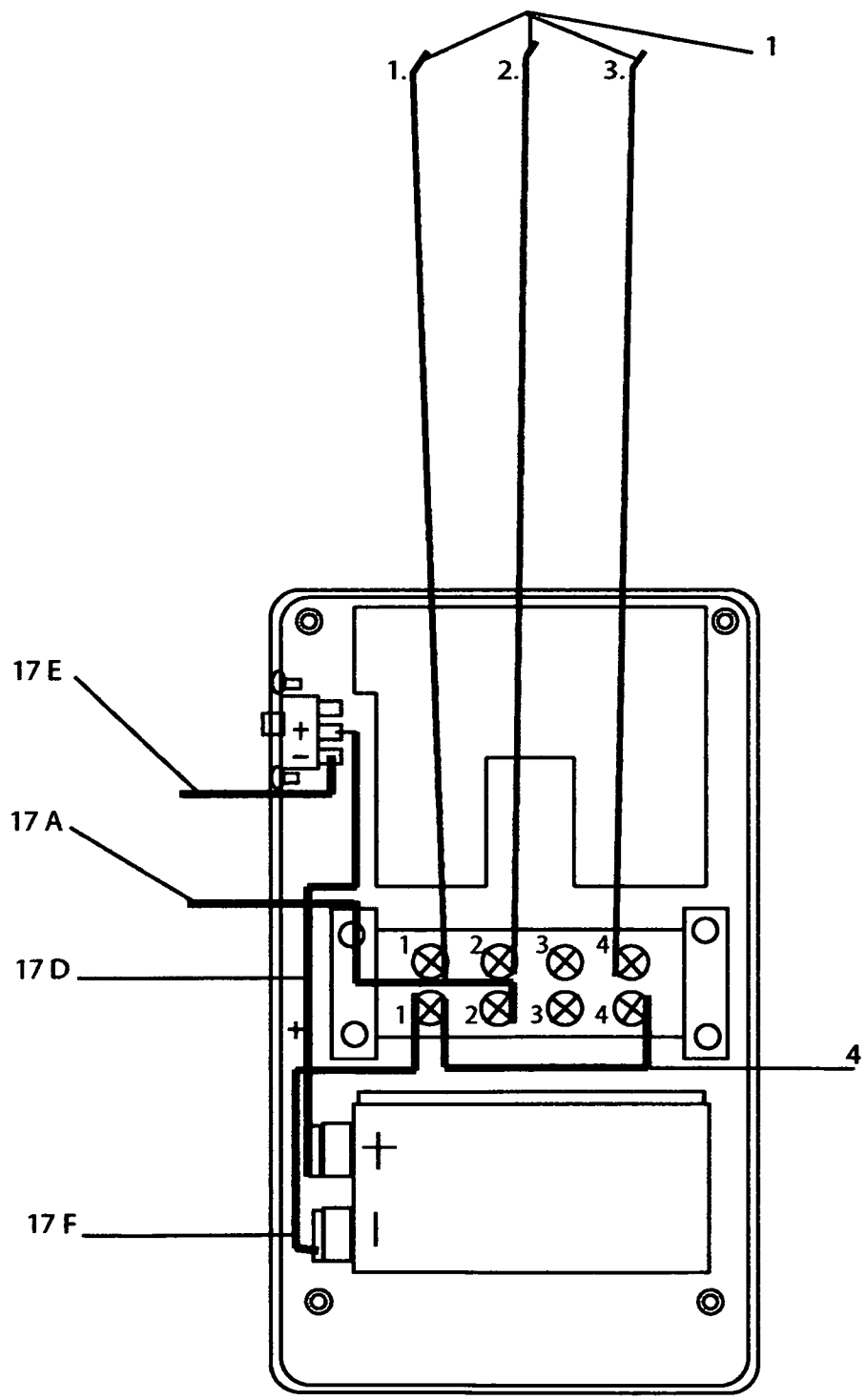
Figure 6A:
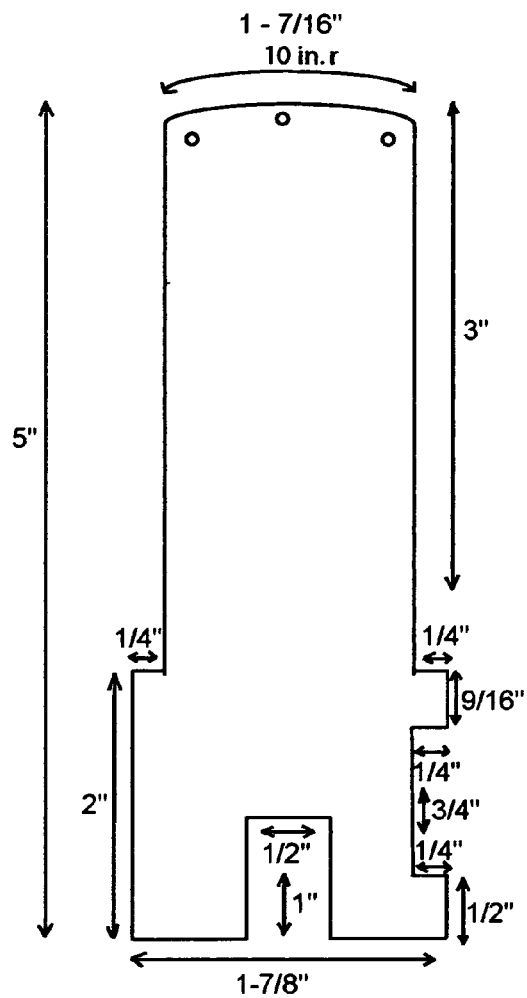
Figure 6B:
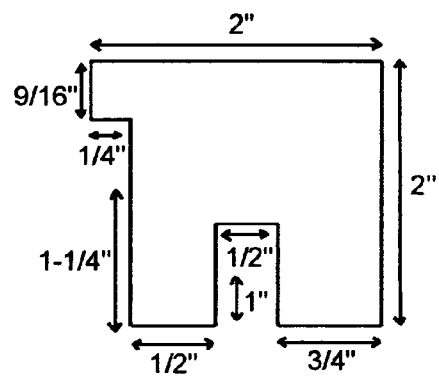

FIG. 1 is a top outside view thereof;
FIG. 2A is a bottom outside view thereof;
FIG. 2B is a bottom view of a battery compartment cover.
FIG. 3 is a side view thereof;
FIG. 4A is a top inside view thereof;
FIG. 4B is a bottom inside view thereof;
FIG. 5 is a bottom inside view wiring thereof;
FIG. 6A is a voltage conduction extension mount dimensions view thereof;
FIG. 6B is a voltage conduction extension mounting block dimensions view thereof;

ADVANTAGES

1. The Tongue Relaxer releases tongue tension far more directly, safer, quicker, and more effectively than all prior art.
2. Said device is portable.
3. Said device is easy to use.
4. Said device may be sterilized for repeated clinical and professional use.
5. Said device only requires only a few seconds to use, and its positive effects are direct, and last for hours, relaxing the deep cramped muscles of said tongue without hidden side effects.
6. Said device is a new means of addressing tongue cramping, and tension.
7. Said device does not require a prescription.
8. Said device is an energy efficient, renewable means of addressing tongue tension.
9. Said device is a sterile and effective means of relieving said tongue tension.

DETAILED DESCRIPTION OF THE INVENTION

FIG. 1 continued:
FIG. 1 Item 22. Shows a top view of a Top fascia label mounting recess. Used to indicate Brand, logo, Name of Product, power, 0-9 volt level labeling for the potentiometer.
FIG. 2A Shows a Bottom outside view of the Tongue Relaxer Housing.
Item 23 Shows the bottom Facia recess intended for applying the bottom label with model patent and bar code information.

FIG. 2B Shows a Battery Compartment Cover which is to be placed over the Battery compartment shown therein FIG. 2A
FIG. 3 Shows a Side view of the Tongue Relaxer.
Item 1 Shows a side parallel view of the Wire Voltage Conductors 1.2.3. Mounted to the Voltage Conducting Extension Mount. The Wire Voltage Conductors transmit low voltage to the areas of the tongue in need of tension release. Said Wire Voltage Conductors are to be composed of medical grade wire and may be easily purchased at any orthodontic and or dental, or medical supply retailer. The dimensions of the Wire Voltage Conductors are no limited to any dimensions. The color of said Wire Voltage Conductors are viable to be manufactured in all colors within the visible spectrum from 390 to 750 nm wavelength nanometers.

DETAILED DESCRIPTION OF THE INVENTION

FIG. 1
Top View:
Shows a Housing. Said Housing dimensions are 5 inches long×2¾ inches wide×1 inch deep when assembled, however is not limited to these shapes and or dimensions.
Said Housing may be easily purchased at any reputable electronic supply retailer.
Said Housing may be, constructed of plastic however is not limited to this material. Other rigid materials may be also used such as aluminum, steel, PVC, nylon etc. . . . . .
The color of said Housing is viable to be manufactured in all colors within the visible spectrum from 390 to 750 nm wavelength nanometers.
FIG. 1 Item 10. Shows a top view of a Potentiometer used for adjusting the level of transmitted voltage from 0-9 volts.
FIG. 1 Item 11. Shows a top view of a Momentary button. When depressed, to momentarily open the circuit thereby allowing the flow of desired voltage to the tongue via Wire Voltage Conductors.
FIG. 1 Item 14. Shows a top view of a Voltage Conduction Extension Mount. Used as a rigid structure on which to mount the Wire Voltage Conductors.
FIG. 1 Item 16. Shows a top view of an On/Off Power switch. Used as a main circuit break.

DETAILED DESCRIPTION OF THE INVENTION: FIG. 3 CONTINUED

Item 10 Shows a side view of the potentiometer and or attenuator which is mounted on the top of the housing can be easily purchased at any reputable electronic supply retailer. Dimensions are ¾" diameter at the base and ⅛" at the top however is not limited to these dimensions. The color of said potentiometer is viable to be manufactured in all colors within the visible spectrum from 390 to 750 nm wavelength nanometers.
Item 11 Shows a side view of the momentary button which is mounted on the top of the housing can be easily purchased at any reputable electronic supply retailer and is not limited to any dimension. The color of said momentary button is viable to be manufactured in all colors within the visible spectrum from 390 to 750 nm wavelength nanometers.
Item 14 Shows a side view of the voltage conduction extension mount. The thickness of the voltage conduction extension mount is to be ¼ inches however is not limited to these dimensions and is to be constructed of food grade and or medical grade rigid plastic however is not limited to this material. Other materials such as surgical plastic, teflon, PVC, nylon or any food grade suitable sterilizable, nonconductive material may be used to construct said voltage conduction extension mount. Material used to construct the voltage conduction extension mount may be easily purchased at any reputable medical supply and or professional kitchen supply retailer. The color of said voltage conduction extension mount is viable to be manufactured in all colors within the visible spectrum from 390 to 750 nm wavelength nanometers.

DETAILED DESCRIPTION OF THE INVENTION: FIG. 3 CONTINUED

Item 16 Shows a side view of the on/off Power Switch which is mounted on the side of the housing can be easily purchased at any reputable electronic supply retailer and is not limited to any dimension. The color of said momentary button is viable to be manufactured in all colors within the visible spectrum from 390 to 750 nm wavelength nanometers.

Item 21 Shows a side view of the housing. Housing can be easily purchased at any reputable electronic supply retailer and is not limited to any dimension. The Housing may be constructed of plastic however is not limited to this material. Other rigid materials may also be used, such as aluminum, steel, zinc, and more. The color of said housing is viable to be manufactured in all colors within the visible spectrum from 390 to 750 nm wavelength nanometers.

DETAILED DESCRIPTION OF THE INVENTION

Top Inside View

FIG. 4A continued:
Item 13 Shows a Voltage Conduction Extension Mount
Item 14 Shows the Wire Voltage Conductor (Mounting Holes) 1.2.3.
Item 15 Shows a Positive Lead wire from Momentary Switch to Terminal 2.
Item 16 Shows a Negative Lead wire from Potentiometer to negative contact of Power Switch
FIG. 4B Shows a Bottom inside view of the Bottom half of Housing therein inner workings: Wiring:
  Item 1—1. Shows a (Negative) Wire Voltage Conductor
  Item 1—2. Shows a (Positive) Wire Voltage Conductor
  Item 1—3. Shows a (Negative) Wire Voltage Conductor
  item 2 Shows a top view of a Voltage Conduction Extension (Mounting Block)
Item 3 Shows a top view of a Terminal Block. A means in which to route wiring.
  Item 4 Jumper Wire (Negative)
Item 5 Shows top inside view of a battery compartment.
FIG. 5 Shows a Bottom inside view of the Bottom half of Housing therein inner workings: Wiring:
  Item 1—1. (Negative) Wire Voltage Conductor
  Item 1—2. (Positive) Wire Voltage Conductor
  Item 1—3. (Negative) Wire Voltage Conductor
  Item 4 Jumper Wire (Negative)

DETAILED DESCRIPTION OF THE INVENTION

FIG. 5 continued:
Item 17A Shows a (Positive) Lead to Terminal Block

Item 17D Shows a (Positive) Lead from On/Off Power Switch to Battery Compartment
Item 17E Shows a (Negative) Lead from On/Off Power Switch
Item 17F Shows a (Negative) Lead from a battery compartment to a Terminal Block
FIG. 6A Shows a VOLTAGE CONDUCTION EXTENSION MOUNT
Top view with Fabrication Dimensions
However are not limited to these shapes and or dimensions. Said Voltage Conducting
Extension Mount protrudes 2¾ inches from the exterior of the Housing.
However is not limited to these shapes and or dimensions.
The thickness of the said Voltage Conducting Extension Mount is to be manufactured at one ¼ inch however is not limited to these dimensions.
Said Voltage Conduction Extension Mount is to be constructed of food grade and or medical sterilizable rigid plastic however is not limited to this material. Material to fabricate said Mount may be easily purchased at any reputable Medical supply and or Professional Kitchen supply retailer. However, other materials such as surgical plastic, teflon, PVC, nylon or any food grade suitable, sterilizable, rigid, nonconductive material may be used for the fabrication of Voltage Conduction Extension Mount. The color of said VOLTAGE CONDUCTION EXTENSION MOUNT is viable to be manufactured in all Colors within the visible spectrum from 390 to 750 nm wavelength nanometers

DETAILED DESCRIPTION OF THE INVENTION

FIG. 6B Shows a Voltage Conductor Extension (Mounting Block) With Fabrication Dimensions. However is not limited to these shapes and or dimensions.
The thickness of the said Voltage Conductor Extension (Mounting Block) is to be manufactured at one ¼ inch however is not limited to these dimensions. Said Mounting Block is the means in which to bind the Wire Voltage Conductors between itself and the Voltage Conductor Extension Mount.
The Voltage Conduction Extension (Mounting Block) is to be constructed of food grade and or medical sterilizable rigid plastic Material to fabricate said Mount may be easily purchased at any reputable Medical supply and or Professional Kitchen supply retailer.
However is not limited to this material. Other materials such as surgical plastic, teflon, PVC, nylon or any food grade suitable, sterilizable, rigid, nonconductive material may be used for the fabrication of the Voltage Conductor Extension (Mounting Block)
How to Make and Use:—Wiring:
FIG. 4A-FIG. 4B
Shows a 5 inch positive wire connected to momentary positive pole and Positive Terminal Block pole 2.
Shows a 5 inch negative wire connected to potentiometer negative pole to on-off switch negative pole.
Shows a 2½ inch positive wire from positive pole on-off switch pole to battery positive pole.
Shows a 2½ inch negative wire from momentary button negative pole to potentiometer negative pole Shows a 2½ inch negative wire from said Terminal Block (Negative) pole 1 to negative battery pole Shows a 2¼ inch negative jumper wire from said Terminal Block (negative) pole 1 to said negative Terminal Block (negative) pole 4.
Said Terminal Pole 3 is not used.

Voltage conductor wires:

Voltage conductor wires. Said wires are to have an OD of 0.040

Although said wires are not limited to this dimension, Two said wires must be cut to the length of 5⅝ inches. One of said wires must be cut to the length of 5¾ inches.

How to Make and Use:—Wiring: continued

Said Voltage conductor wires must be bent on both ends at a one ¼ inch length.

Said wires must be bent at 90 degree angles.

Said wires must all be bent facing upward on one end.

The opposing ends of Two said wires must be bent at a 90 degree angles of Voltage conductor wires opposing end.

One wire at 90 degrees toward the left and the other said wire at 90 degrees toward the right. Note: The remaining center Positive Voltage Conductor Wire must have a plastics wire insulator slipped on BEFORE the final 90 degree bend is made. The insulator measures 1 inch in length, said wire insulator has an ID of 0.040 and an OD of 0.090.

Said wire must then be bent at a left 90 degree angle on said wires opposing end in preparation for mounting on said Terminal Block.

Connect both Negative voltage conductor wires to both Negative terminal pole 1 must have a 90 degree bend facing left held fixed by means of screws on said terminal block.

Pole 4 must have a 90 degree bend facing right held fixed by means of sandwiching screws on said terminal block.

Connect the Positive voltage conductor wire to the Positive terminal

Pole 2. With said 90 degree bend facing left held fixed means of sandwiching screws on said terminal block. Said wires opposing ends must be upward facing and are to be inserted into the respective Wire Voltage Conducting Mounting Holes. FIG. 5 1 2 3 upon final assembly of Housing.

Conclusion, Ramifications, Scope, Detail Description:—How to Make and Use.

Said Tongue relaxer is a very mild but effective direct therapy apparatus.

A new, and unique means of physical therapy for the tongue.

All dimensions colors and forms of said Tongue relaxer may be increased, decreased, and altered in form without limitation.

The advantages of said Tongue relaxer are many.

Said Tongue relaxer is completely portable, small and very easy to use.

Said Tongue relaxer is very quick, and effective enabling both physician, a speech therapist, professional singer, actor, teacher, public speaker, to administer to or to self administer this therapy, either in the office or in the field.

Said Tongue relaxer is completely non allergenic. There is no risk of any allergic reactions.

Said Tongue relaxer is a very clean way of applying a unique physical therapy.

All parts that will come in contact with the mouth are durable and easy to sterilize, Maintenance is quite easy. One only needs to sterilize orally contacting parts in between uses, and change a 9 volt battery when needed.

They are no prescriptions to refill. No food items to have to keep, or bags of herbal remedies to constantly replenish and keep on hand.

Conclusion, Ramifications, Scope, Detail Description:—How to Make and Use.

Said Tongue relaxer is always ready to use and requires very low power consumption. Said Tongue relaxer will last for years, verses all prescriptions and temporary herbal, and or consumable remedies. Said Tongue relaxer is far quicker and effective than traditional approaches to tension in the muscles of the tongue. Said Tongue relaxer directly addresses a main root cause of many related speech and vocalization disorders allowing freedom and range of motion to be reestablished enabling said Speech therapist, Voice trainer to begin to reestablish with said patient correct speaking and singing habits and furthermore more refined techniques. Thus being a significant contributor to the arts. Said Tongue relaxer's unique, and sterile, renewable means of therapy which proves to be far more efficient that prior approaches attempting to correct bad habits all the while the patient is still battling restrictions of sever tongue tension. This prior traditional approach is very time consuming, detrimental and counter productive. Such approaches force the patient to generalize due to sever, inherent restrictions. Refined speech and or singing then becomes very difficult to establish and therefore maintained by this said traditional prior means of approach.

Therapists must always first gain full mobility, flexibility and range of motion within the deep muscles of the tongue with a patient before attempting to develop refined strength and skill. Otherwise you will only generalize said patients development without realizing said patient's full potential of refined skill development.

Said Tongue relaxer enables said patient to begin again either speaking or singing with a new beginning, uninhibited by prior said limiting tensions.

Conclusion, Ramifications, Scope, Detail Description:—How to Make and Use.

Voltage Extension Mount: FIG. 6A must be cut from ¼ inch thick medical and or food grade rigid plastic according to the dimensions as illustrated in FIG. 6A

Voltage Conduction Extension (Mounting Block): FIG. 6B must be cut from ¼ inch thick medical and or food grade rigid plastic according to the dimensions as illustrated in FIG. 6B

Wire Voltage Conductor Mounting Holes: FIG. 4A (Top Inside View) Items 14—1. 2. 3. Must be drilled according to said holes appropriate positions in accordance the lengths and positions coordinated with each said hole's respective Wire Voltage Conductor to be inserted later.

Wire Voltage Conductors: Preparation

FIG. 4B items 1—(1 2 3)

Said Tongue Relaxer has 3 rigid. Medical grade wires.

Voltage conductor wires. Said wires are to have an OD of 0.040

Although said wires are not limited to this dimension, Two said wires 1. 3. Must be cut to the length of 5⅝ inches.

Said wire 2. Must be cut to the length of 5¾ inches.

Said Voltage conductor wires must be bent on both ends at a one ¼ inch lengths.

And must be bent at 90 degree angles.

Conclusion, Ramifications, Scope, Detail Description:—How to Make and Use.

Said wires must all be bent facing upward on the end of said Wire Voltage Conductor Mounting Holes of said Wire Voltage Conduction Extension Mount in preparation for final assembly.

The opposing ends of said wires (1. 2. 3.) Must be bent at a 90 degree angles.

Bend said wires 1. 2. 90 degrees toward the left of the said Terminal Block end.

Note: Said wire 2. (center) Positive Voltage Conductor Wire must have a plastic wire insulator slipped on BEFORE the final 90 degree bend is made on said Terminal Block end.

Said insulator measures 1 inch in length, said wire insulator has an inside diameter of 0.040 and an outside diameter of 0.090.

The remaining said wire 3, is bent a 90 degrees toward the right of the said Terminal Block end. Said wire 3 must then be bent at a 90 degree angle towards the right in preparation for mounting on said Terminal Block.

Housing: FIG. 3 Item 21 must be placed as shown in FIG. 4A and FIG. 4B

Terminal Block:

FIG. 4B item 3. Shows a Terminal Block.

Said Terminal Block can be easily purchased at any reputable electronic supply retailer.

Said Terminal Block is the means to route and interconnect said voltage to said Wire voltage conductors.

Said Terminal Block must be adhered with professional grade adhesive to the inside of said Housing illustrated in FIG. 4B Conclusion, Ramifications, Scope, Detail Description:— How to Make and Use.

Voltage Conduction Extension (Mounting Block):

FIG. 4B Item 2. must be adhered by means of adhesive to the inside of said Housing as illustrated in FIG. 4B On-Off Switch: FIG. 1 Item 16 FIG. 3 Item 16 and FIG. 4B can be easily purchased at any reputable electronic supply retailer. Said On-Off Switch must be mounted on the side of said housing as illustrated in FIG. 4B Potentiometer: can be easily purchased at any reputable electronic supply retailer.

Said Potentiometer must be mounted on the top of said Housing as illustrated in FIG. 1 Item 10 FIG. 3 Item 10, and FIG. 4A Item 10

Momentary Button: can be easily purchased at any reputable electronic supply retailer.

Said Momentary Button must be mounted on the top of said Housing as illustrated in FIG. 1 Item 11 FIG. 4, and FIG. 3 Item 11

Wiring: Connect all wiring by means of solder or quick connects as illustrated in FIG. 4A and FIG. 4B Wire Voltage Conductors: assembly FIG. 4B items 1—(1 2 3) FIG. 5 items 1—(1 2 3) FIG. 3 item 1

Attach said Wire Voltage Conductors as illustrated in FIG. 4B and FIG. 5 Said wires must be positioned as such so that the opposing ends of the said Terminal Block are facing upward. Housing: final assembly Conclusion, Ramifications, Scope, Detail Description:— How to Make and Use.

Carefully Join together both top, and bottom half's of said Housing thereby sandwiching said Wire Voltage Conducting Wires. Carefully aligning and inserting said Wire Voltage Conductors in accordance to their respective said Wire Voltage Conducting Mounting Holes as illustrated in FIG. 4A Item 1—1. 2. 3.

(Medical and or dental grade adhesive must be applied inside said Wire Voltage Conducting Mounting Holes before insertion of Wire Voltage Conductors) upon final assembly.

Said adhesive may be easily purchased from any reputable Medical and or dental supply retailer. Upon said final assembly, confirm final inspection comparing to: FIG. 1 (Top Outside View), FIG. 2A and FIG. 3 (Side View)

Preparation for Operation: Place a common 9 volt battery inside the back of said Housing as illustrated in FIG. 2A. Said battery may be purchased at any pharmacy and or wholesale battery reseller. Place Battery Compartment Cover: FIG. 2B on the back of said Housing.

Carefully Join together both top, and bottom half's of said Housing thereby sandwiching said Wire Voltage Conducting Wires. Carefully aligning and inserting said Wire Voltage Conductors in accordance to their respective said Wire Voltage Conducting Mounting Holes as illustrated in FIG. 4A Items 1—1.2.3. and FIG. 4A Items 14—1.2.3.

(Medical and or dental grade adhesive must be applied inside said Wire Voltage Conducting Mounting Holes before insertion of Wire Voltage Conductors) upon final assembly.

Said adhesive may be easily purchased from any reputable Medical and or dental supply retailer.

Conclusion, Ramifications, Scope, Detail Description:— How to Make and Use.

Upon said final assembly. Inspect, and confirm by final inspection examining and comparing to: FIG. 1 (Top Outside View), FIG. and FIG. 3 (Side View)

Preparation for Operation:

Place a common 9 volt battery inside the back of said Housing as illustrated in FIG. 2.

Said battery may be purchased at any pharmacy and or wholesale battery reseller.

Place Battery Compartment Cover: FIG. 3 on the back of said Housing.

How to Use

First Embodiment

This device is a convenient, self contained, portable, handheld embodiment.

Said device has been designed to release unwanted tension in the deep muscles of the tongue and related throat muscles. Said device is to be held in the hand of either a physician or patient, user. A momentary button, and a potentiometer are positioned conveniently on top of said embodiment. A power button is conveniently located on the side of said embodiment and must be switched to the on position. Said device is now ready for operation. Said potentiometer is to be Turned counter clockwise. All the way to the off position. A flat sterile, protrusion extending from said embodiment which has three conduction wires must be facing downward, extending the length of said extension.

Said extension is to be positioned as to align inwardly said wires with the body of said tongue, resting upon the middle and sides of said body of said tongue.

Said physician or patient will then place said protrusion upon the body of the tongue, with wires facing downward as to be in contact with said body of the tongue.

Conclusion, Ramifications, Scope, Detail Description:— How to Make and Use.

Said physician or said patient, user will then press said momentary button down, then release quickly disengaging said voltage.

This process is then repeated incrementally as a test pulse.

Gradually, said user is to turn said potentiometer clockwise to the right, increasing the amount of voltage administered to the body of said tongue until reaching said patients desired amount. Said patient should experience a firm but comfortable pulsing sensation being transmitted into the deep muscles of said body of said tongue.

Once this is established.

Said physician, or patient, user will give approximately three to four pulses, held approximately for the duration of 1 second each, administered to the areas of said tongue most in need of said muscle tension release.

Note: Even upon said device being turned all the way up to the maximum setting, said voltage is still very tolerable, and safe. Said device is a very mild but effective direct therapy.

Said device is a new and unique as a means of physical therapy for the tongue

I claim:

1. A portable therapeutic substitutionary device adapted to stimulate the tongue for providing an alternative to conventional muscle relaxation for a subject comprising:
   a) a extension mount adapted to be received into the mouth of the subject;
   b) a series of three elongated voltage conductors positioned over a lower surface of the extension mount adapted to be in contact with the full length of tongue when the extension mount is received into the mouth;
   c) a potentiometer means for manually controlling the level of electrical voltage transmitted to said tongue;
   d) a momentary button for depressing means for temporarily opening a circuit for transmitting a stimulating electrical signal from an excitation circuit to the top surface of said tongue, whereby upon releasing interrupts the electrical signal to said subject's tongue;
   e) an on-off switch for opening and closing a main circuit from a battery.

2. The therapeutic substitutionary device as recited in claim 1, wherein said device further comprises a means for providing momentary electrical impulses, in order to provide immediate relief from muscle tension at the root of said tongue.

3. The therapeutic substitutionary device as recited in claim 1, wherein said device is battery powered and comprises a housing for holding a battery in communication with said excitation circuit.

* * * * *